United States Patent
Sisney

(10) Patent No.: US 12,167,740 B2
(45) Date of Patent: Dec. 17, 2024

(54) METHOD OF TREATING MEAT

(71) Applicant: Avure Technologies Incorporated, Middletown, OH (US)

(72) Inventor: Gary Sisney, Windsor, CO (US)

(73) Assignee: Innovative Meat Solutions, LLC, Windsor, CO (US)

(*) Notice: Subject to any disclaimer, the term of this patent is extended or adjusted under 35 U.S.C. 154(b) by 354 days.

(21) Appl. No.: 16/462,810

(22) PCT Filed: Sep. 26, 2017

(86) PCT No.: PCT/US2017/053446
§ 371 (c)(1),
(2) Date: May 21, 2019

(87) PCT Pub. No.: WO2018/097887
PCT Pub. Date: May 31, 2018

(65) Prior Publication Data
US 2019/0373922 A1    Dec. 12, 2019

Related U.S. Application Data

(60) Provisional application No. 62/515,587, filed on Jun. 6, 2017, provisional application No. 62/425,454, filed on Nov. 22, 2016.

(51) Int. Cl.
*A23L 3/015*    (2006.01)
*A23B 4/20*    (2006.01)
(Continued)

(52) U.S. Cl.
CPC .............. *A23L 3/0155* (2013.01); *A23B 4/20* (2013.01); *A23L 13/428* (2016.08); *A23L 13/52* (2016.08); *A23L 13/60* (2016.08); *A23V 2002/00* (2013.01)

(58) Field of Classification Search
CPC . A23B 4/20; A23B 4/00; A23L 13/428; A23L 3/0155; A23L 13/60; A23L 13/52; C07K 14/805

See application file for complete search history.

(56) References Cited

U.S. PATENT DOCUMENTS 3,073,700 A    1/1963    Ziegler
2014/0193547 A1    7/2014    Brown et al.

FOREIGN PATENT DOCUMENTS

CA    606 834 A    10/1960
CN    1602737 A    4/2005
(Continued)

OTHER PUBLICATIONS

Jack Appiah Ofori and Yun-Hwa Peggy Hsieh The Use of Blood and Derived Products as Food Additives https://cdn.intechopen.com/pdfs/28918/InTech-The_use_of_blood_and_derived_products_as_food_additives.pdf (Year: 2012).*

(Continued)

*Primary Examiner* — Vera Stulii
(74) *Attorney, Agent, or Firm* — James E. Walton

(57) ABSTRACT

A method of treating meat includes the steps of applying hemoglobin to the meat and pressure treating the meat by application of pressure to the meat at sufficiently high pressure and for a duration of time sufficient to rupture the cell walls of at least some microorganisms present in the meat. The method preserves the natural color of the meat, while eliminating pathogens and bacteria in the meat.

16 Claims, 7 Drawing Sheets

(51) Int. Cl.
    *A23L 13/40* (2023.01)
    *A23L 13/50* (2016.01)
    *A23L 13/60* (2016.01)

(56) References Cited

FOREIGN PATENT DOCUMENTS

| CN | 102647912 A | 8/2012 |
|---|---|---|
| JP | 2014520554 A | 8/2014 |
| WO | 2005/070238 A1 | 8/2005 |
| WO | 2011/038245 A1 | 3/2011 |

OTHER PUBLICATIONS

Thomas E. Creighton, Proteins: Structures and Molecular Properties, 117-23 (W.H. Freeman & Co. 1984).*
Campus, M., "High Pressure Processing of Meat, Meat Products and Seafood," Food Engineering Reviews 2(4):256-273, 2010.
International Preliminary Report on Patentability mailed Feb. 11, 2019, issued in corresponding International Application No. PCT/US2017/053446, filed Sep. 26, 2017, 5 pages.
International Search Report and Written Opinion mailed Dec. 8, 2017, issued in corresponding International Application No. PCT/US2017/053446, filed Sep. 26, 2017, 6 pages.
Jung, S., et al., "Influence of High Pressure on the Color and Microbial Quality of Beef Meat," Lebensm.-Wiss. u.-Technol. 36(6):625-631, 2003.
Polo, J., et al., "The Use of Spray-Dried Animal Plasma in Comparison With Other Binders in Canned Pet Food Recipes," Animal Feed Science and Technology 154:241-247, 2009.
Extended European Search Report and Written Opinion mailed May 18, 2020, issued in corresponding European Application No. 17 87 4761.4, filed Sep. 26, 2017, 11 pages.
Office Action with Search Report mailed Nov. 19, 2020, issued in Chilean Patent Application No. 2019-01377, filed May 22, 2019, 25 pages including translation.
Office Action mailed May 25, 2021, issued in Japanese Patent Application No. 2019-528452, filed May 22, 2019, 7 pages.
Office Action mailed May 10, 2021, issued in Chilean Patent Application No. 2019-01377, filed May 22, 2019, 11 pages.
Office Action mailed Aug. 4, 2021, issued in corresponding AU Application No. 2017363443, filed Sep. 26, 2017, 4 pages.
Preliminary Office Action Report received Dec. 16, 2021, issued in corresponding BR Application No. 112019010428-3, filed Sep. 26, 2017, 3 pages (English translation).
Office Action mailed Jan. 21, 2022, issued in corresponding CN Application No. 201780082688.4, filed Sep. 26, 2017, 12 pages.
Decision of Refusal mailed Feb. 1, 2022, issued in corresponding JP 2019-528452, filed Sep. 26, 2017, 2 pages.
Haifeng, Z., et al., "Application of Superhigh Pressure in Meat Industry," Journal of Agricultural Sciences 30(2): 61-64, Jun. 2009, with English abstract.
Office Action mailed Dec. 30, 2021, issued in corresponding VN Application No. 1-2019-03273, filed Sep. 26, 2017, 3 pages.

* cited by examiner

Sample #1 control, top left
Sample #2 no additive, top right
Sample #3 ½ % dry additive, bottom left
Sample #4 ½ % wet additive, bottom right Top left
Sample #1 Control No HPP or Additive Top right
Sample #2 HPP and No Additive Bottom Left
Sample #3 HPP with 1% additive dry Sample #4 HPP with ½% additive wet Sample 1

Sample 2

Sample 3

METHOD OF TREATING MEAT

TECHNICAL FIELD

The present invention relates generally to methods for improving the color of pressure-treated meat products.

DESCRIPTION OF THE PRIOR ART

The color of fresh meat is one the most important evaluation parameters consumers use when purchasing. For many years, high-pressure processing (HPP) has been used to eliminate pathogens and harmful bacteria in many food and beverage products. HPP is the application of isostatic pressure to a product sealed in a container ("vacuum packed" or "vacuum sealed") and submerged in water at pressures between about 50 and 100,000 pounds per square inch (psi), and typically about 87,000 psi, for varying times, is used to destroy harmful pathogens and bacteria.

As explained by the Food Safety Inspection Service (FSIS) of the U.S. Department of Agriculture (USDA) in directive 6120.1:

HPP subjects food to elevated pressures, with or without the addition of heat, to inactivate microorganisms and extend microbiological shelf life. Product processed with HPP is placed in a sealed flexible container. The flexible container is placed in a basket or barrel and moved to a high-pressure chamber filled with a pressure-transmitting fluid, usually water that does not contact product. The chamber is equipped with pumping and decompression systems. The action of the high pressure causes the microorganism cell walls to rupture resulting in injury or death. Depending upon length of time the product is subjected to pressure, some or all of the microorganisms might be affected. In addition, changes in the product could occur such as distortion of the shape of the product, as well as reduction in its capacity to retain moisture (purge) because of the rupture of the cell walls.

Thus, HPP can be summarized as pressure treating meat by application of pressure to the meat at a sufficiently high pressure, a selected and controlled temperature, and for a duration sufficient to rupture the cell walls of at least some microorganisms present in the meat. HPP is applied to both fresh or raw and cooked or cured meat products, including ready-to-eat products.

The principal advantage of products that have been treated with HPP is longer shelf life—up to 2-4 times that of untreated products. Extending shelf life results in less food waste and more time to market products. Further, USDA considers HPP a "lethality step" per the FSIS directive 6120.1. Products exposed to a lethality step may be exempt from some labeling exemptions and regulations. These exemptions result in cost savings and competitive advantages.

HPP eliminates pathogens such as *e.coli, salmonella* and *listeria*, among others and provides food safety benefits. Because HPP destroys microorganisms which cause spoilage, the flavor profile is extended as well.

Despite all of its advantages, one of the characteristics of meat that has been through HPP is that the meat changes color. In ready-to-eat meats, this color change is not very noticeable, but in others the color change is more severe. Ground meat has been one of the items that the color is changed so much that the consumers have not accepted it. The color of fresh ground beef is much lighter shade of red almost pink or opaque in some cases. Because most consumers buy ground beef based on appearance and the color of the meat is a determining factor of their perception of lean content, HPP ground meats have not met consumers' expectations in regards to color.

Many have tried to add ingredients and made adjustments to temperature of water and product, time under pressure and varying pressure settings to eliminate or minimize the color change without much success.

BRIEF DESCRIPTION OF THE DRAWINGS

The priority documents for this application contain color drawings and/or color photographs, which are incorporated herein by reference for all purposes, including entry into the National Stage in those countries that accept color drawings and/or photographs. Copies of this patent application publication with color drawing(s) will be provided upon request and payment of the necessary fee.

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
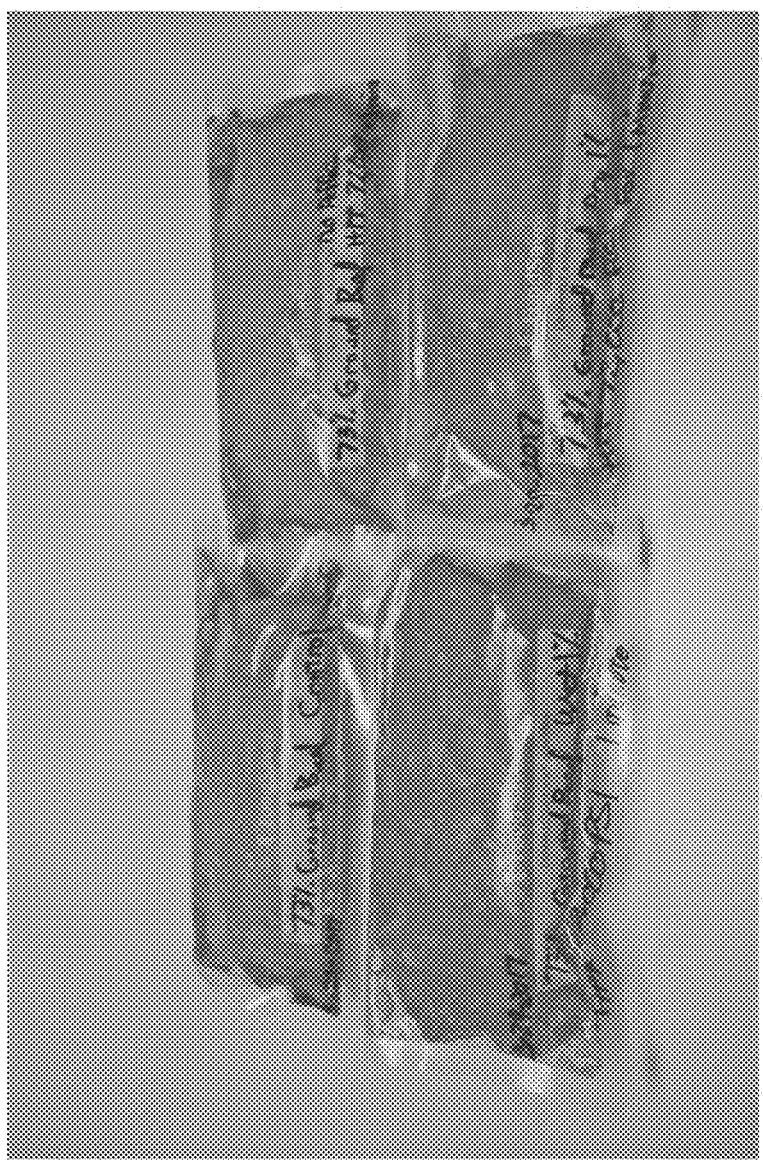
FIG. 1 is a photograph showing the results of Example I.

Although the pressure values in accompanying drawings are labeled as "PSI," it will be understood that the values for the pressure are actually in KPSI, as referred to in the written description. In addition, the photographs used in FIGS. 1-4 are representative of the results from using either porcine hemoglobin or bovine hemoglobin in carrying out the procedures according to the present application.

While the method of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, combinations, and alternatives falling within the spirit and scope of the present application as defined by the appended claims.

DESCRIPTION OF THE PREFERRED EMBODIMENT

Illustrative embodiments of the disclosed method for improving the color of HPP-treated meat products are provided below. It will of course be appreciated that in the development of any actual embodiment, numerous implementation-specific decisions will be made to achieve the developer's specific goals, such as compliance with assembly-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The color of HPP-treated meat products may be improved by the addition of hemoglobin, which may or may not contain red blood cells, to the meat prior to or during HPP treatment. According to one embodiment of the invention, about 0.08% to about 3.0% by weight of hemoglobin is mixed or kneaded into raw meat before HPP treatment. The percentage by weight of hemoglobin will vary depending on the desired color. As the percentage is increased the color will increase in a darker color, until desired color is achieved.

A lesser percentage of hemoglobin may be added to larger quantities, by weight, of meat or to whole-muscle meats. It may be manually or mechanically mixed with the meat or topically applied. The hemoglobin may be added to the meat in liquid form, sprayed dried, freeze dried or otherwise processed into a powdered form and mixed with the meat, or hydrated with water to form a slurry and mixed with the meat.

The hemoglobin may be added as a separate processing step prior to HPP treatment or may be incorporated into HPP processing itself. That is, the hemoglobin, alone or with spices, may be mechanically mixed or applied to the meat prior to placing it in a sealed, flexible container, which is in turn HPP processed, or, the hemoglobin could be placed in the sealed, flexible container with the meat.

Hemoglobin may be applied to beef, bison, lamb, pork, veal, chicken, turkey, or other poultry, or fish or other seafood, or any meat subject to HPP processing. The meat may be fresh (raw) or cooked or cured or spiced. The meat may be ground or processed or whole muscle meat.

Hemoglobin is a pigment material derived from animal blood, which may or may not contain red blood cells. Whole animal blood has many components and these components can be separated by centrifuge equipment or filters. As an example typically whole blood is separated by centrifuge into red blood cells and plasma, the red blood cells can then be separated from the hemoglobin by filtration. As an example, it is commercially available from Sonac Loenen BV, Kanaaldijk Noord 20, 5691 NM, P.O. Box 9, 5690 AA Son, The Netherlands. It is available in a "stabilized" powder form, Hemoglobin powder 92P, derived by spray drying from porcine blood without active additives. It is also available from Sonac under the "Harimix" brand name mixed with various additives, such as sugar, salt, water, sodium ascorbate, and citric acid. Available from Sonac also is Harimix PB "stabilized" powder hemoglobin derived from bovine blood. The stabilized powder form, without other active ingredients or additives, is preferred, but hemoglobin with additives may be optimal, dependent upon the particular application. Hemoglobin may be derived from the blood of the same species as the meat being treated or from a different species. Dried hemoglobin is also available from Essentia Proteins Solutions, headquarters at 2425 SE Oak Tree Ankeny, Iowa 50021 USA under the trade AproRED.

Hemoglobin powder may be kneaded into the meat (for ground meat), applied to the surface of the meat (for muscle meat), or otherwise incorporated in the meat, until the surface of the meat is coated and a homogeneous blend and color is achieved. Hemoglobin powder may be hydrated with water and similarly mixed with the meat. Hemoglobin powder may be hydrated and frozen for storage and then thawed and similarly mixed with or applied to the meat. Hemoglobin in liquid form may be mixed with or applied to the meat with or without freezing for storage and thawing. Hemoglobin or red blood cells may be applied in a non-processed form to achieve similar results.

EXAMPLES

The following examples are provided by way of illustration of embodiments of the invention and are not intended to limit or constrain the invention. As set forth above, porcine hemoglobin and bovine hemoglobin may be interchanged in the examples below, either one producing very similar results, as represented by FIGS. 1-7. Other sources of animal hemoglobin may also be used and may also provide similar results.

Example I

Four samples, each of 200 grams of 73% lean ground beef, were prepared as follows:

Sample 1. Control sample, No (0% by weight) dried hemoglobin powder added and no high pressure processing.

Sample 2. No (0% by weight) dried hemoglobin powder.

Sample 3. 1% by weight (2 gram) dried bovine hemoglobin powder Sonac Harimix PB manually kneaded into meat.

Sample 4. 1.0% by weight (2 grams) hydrated bovine hemoglobin powder Sonac

Harimix PB manually kneaded into meat.

Each sample was vacuum sealed in a polymer package. Samples 1, 3, and 4 were then subjected to HPP treatment in an Avure QFP 525L-600 HPP apparatus at about 72,000 psi and a temperature of about 38-40 degrees Fahrenheit for 60 seconds. Sample 1 was not HPP treated. The resulting packages are shown in FIG. 1. As can be visually seen, samples 1, 4 and 3 exhibit similar bright red color, while sample 2 without addition of dried hemoglobin powder is visibly lightened to pink.

Each sample's color was checked and recorded using a Hunter Mini Scan XE spectrophotometer:

| Sample #1 readings | L* | 46.46 | A* | 8.02  | B* | 14.57 |
| Sample #2 readings | L* | 52.14 | A* | 5.99  | B* | 18.65 |
| Sample #3 readings | L* | 44.96 | A* | 15.54 | B* | 15.99 |
| Sample #4 readings | L* | 49.90 | A* | 12.65 | B* | 15.57 |

Example II

Four samples, each of 200 grams of 93% lean ground beef, were prepared as follows:

Sample 1. Control sample #1, No (0% by weight) dried bovine hemoglobin powder added and no high pressure processing.

Sample 2. No (0% by weight) dried hemoglobin powder.

Sample 3. 0.5% by weight (1 gram) dried bovine hemoglobin powder Sonac Harimix PB manually kneaded into meat.

Sample 4. 0.5% by weight (1 gram) hydrated dry bovine hemoglobin powder Sonac Harimix PB manually kneaded into meat.

Figure 2:
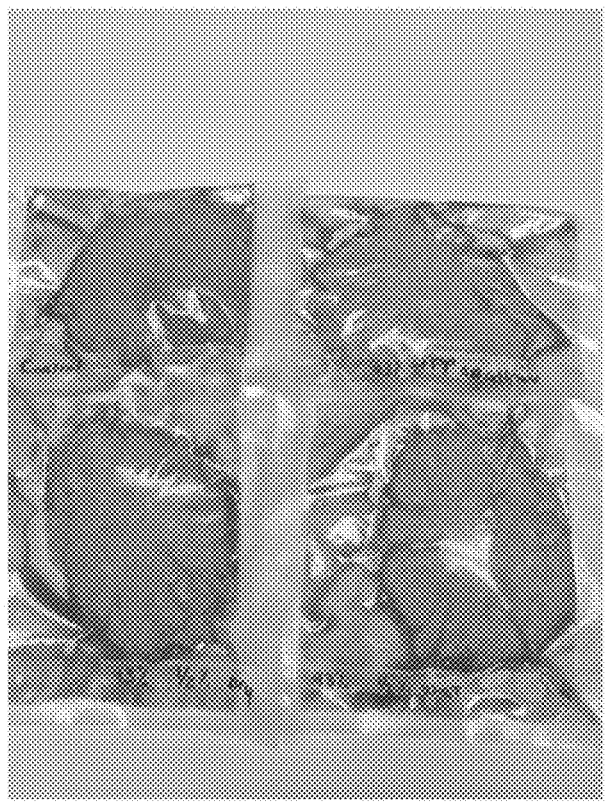
FIG. 2 is a photograph showing the results of Example II.

Each sample was vacuum sealed in a polymer package. Samples 2, 3, and 4 were then subjected to HPP treatment in an Avure QFP 525L-600 apparatus at about 86,000 psi and a temperature of about 38-40 degrees Fahrenheit for about 180 seconds. Sample 1 the control was not HPP treated. The resulting packages are shown in FIG. 2. As can visually be seen, samples #1,#3 and #4 exhibit similar bright red colors while sample #2 is without addition of dried hemoglobin powder is visibly lightened in color.

Each sample's color was checked and recorded using a Hunter Mini Scan XE spectrophotometer:

| | | | | | | | |
|---|---|---|---|---|---|---|---|
| Sample #1 readings | L* | 37.84 | A* | 14.05 | B* | 14.41 |
| Sample #2 readings | L* | 49.43 | A* | 11.26 | B* | 15.47 |
| Sample #3 readings | L* | 39.76 | A* | 17.78 | B* | 15.94 |
| Sample #4 readings | L* | 38.50 | A* | 15.90 | B* | 15.29 |

Example III

Four samples, each of 200 grams of 80% lean chuck ground beef, were prepared as follows:
Sample 1. Control sample, NO dried hemoglobin powder added and No HPP.
Sample 2. No (0% by weight) dried hemoglobin powder.
Sample 3. 1.0% by weight (2 gram) dried bovine hemoglobin powder Sonac Harimix PB manually kneaded into meat.
Sample 4. 0.50 by weight (1 gram) hydrated dried hemoglobin powder.

Figure 3:
FIG. 3 is a photograph showing the results of Example III.

Each sample was vacuum sealed in a polymer package. Samples 2, 3, and 4 were then subjected to HPP treatment in an Avure QFP 525L-600 apparatus at about 72,000 psi and a temperature of about 38-40 degrees Fahrenheit for 60 seconds. Sample 1 was not HPP treated. The resulting packages are shown in FIG. 3. As can be seen, sample 1 exhibit bright red color, while sample 2 is visibly lighter than sample 1, 3, and 4. While samples 3 and 4 having additive show to much darker red color.

Each sample's color was checked and recorded using a Hunter Mini Scan XE spectrophotometer:

| | | | | | | |
|---|---|---|---|---|---|---|
| Sample #1 readings | L* | 36.74 | A* | 7.35 | B* | 13.54 |
| Sample #2 readings | L* | 44.97 | A* | 4.40 | B* | 16.09 |
| Sample #3 readings | L* | 30.65 | A* | 12.46 | B* | 15.83 |
| Sample #4 readings | L* | 34.82 | A* | 12.77 | B* | 16.03 |

Example IV

Three samples, each of 200 grams of boneless pork chop, were prepared as follows:
Sample 1. No (0% by weight) dried hemoglobin powder.
Sample 2. No (0% by weight) dried hemoglobin powder.
Sample 3. 0.08% by weight (0.16 gram) dried porcine hemoglobin powder Sonac Harimix 92 P topically applied.

Figure 4:
FIG. 4 is a photograph showing the results of Example IV.

Each sample was vacuum-sealed in a polymer package. Samples 2 and 3 were then subjected to HPP treatment in an Avure QFP 525L-600 apparatus at about 72,000 psi and a temperature of about 38-40 degrees Fahrenheit for 60 seconds. Sample 1 was not HPP treated. The resulting packages are shown in FIG. 4. As you can see sample 1 has a darker natural meat color, sample 2 color is opaque almost white while sample 3 is a darker natural meat color as opposed to sample 2 and slightly lighter than sample 1.

Each sample's color was checked and recorded using a Hunter Mini Scan XE spectrophotometer:

| | | | | | | |
|---|---|---|---|---|---|---|
| Sample #1 readings | L* | 38.14 | A* | 6.30 | B* | 3.48 |
| Sample #2 readings | L* | 69.42 | A* | 0.29 | B* | 10.53 |
| Sample #3 readings | L* | 46.14 | A* | 7.21 | B* | 8.22 |

Example V

Three samples, each of 200 grams of Italian pork sausage King Soopers™ brand, were prepared as follows:
Sample 1. No (0% by weight) dried hemoglobin powder.
Sample 2. No (0% by weight) dried hemoglobin powder.
Sample 3. 0.5% by weight (1 gram) dried porcine hemoglobin powder Sonac Harimix 92P manually kneaded into meat.

Figure 5:
FIG. 5 is a photograph showing the results of Example V.

Each sample was vacuum-sealed in a polymer package. Samples 2 and 3 were then subjected to HPP treatment in an Avure QFP 525L-600 apparatus at about 72,000 psi and a temperature of about 38-40 degrees Fahrenheit for 60 seconds. Sample 1 was not HPP treated. The resulting packages are shown in FIG. 5. As you can see, sample 1 has a natural meat color, sample 2 has a lighter color, and sample 3 is a darker natural meat color than sample 2.

Each sample's color was checked and recorded using a Hunter Mini Scan XE spectrophotometer:

| | | | | | | |
|---|---|---|---|---|---|---|
| Sample #1 readings | L* | 41.58 | A* | 2.61 | B* | 10.30 |
| Sample #2 readings | L* | 46.93 | A* | 0.28 | B* | 9.73 |
| Sample #3 readings | L* | 43.76 | A* | 4.19 | B* | 13.67 |

Example VI

Four samples each of 200 grams of Pork Breakfast Sausage Kroger (TM) brand, were prepared as follows:
Sample 1. No (0% by weight) dried hemoglobin powder.
Sample 2. 1.0% by weight (2.0 grams) dried porcine hemoglobin powder Sonac Harimix PP hydrated with 1 gram of water mixed and then manually kneaded into meat.
Sample 3. 0.5% by weight (1 gram) dried porcine hemoglobin powder Sonac Harimix PP manually kneaded into meat.
Sample 4. No (0% by weight) dried hemoglobin.

Figure 6:
FIG. 6 is a photograph showing the results of Example VI.

Each sample was vacuum-sealed in a polymer package. Samples 2, 3 and 4 were then subjected to HPP treatment in an Avure QFP 525L-600 apparatus at about 72,000 psi and a temperature of about 38-40 degrees Fahrenheit for 60 seconds. Sample 1 was not HPP treated. The resulting packages are shown in FIG. 6. As you can visually see sample 1 has a natural meat color, sample 2 has a similar natural meat color, sample 3 is a lighter natural meat color than sample 2, sample 4 has a much lighter opaque color with little to no red pigment color.

Each sample's color was checked and recorded using a Hunter Mini Scan XE spectrophotometer:

| | | | | | | |
|---|---|---|---|---|---|---|
| Sample #1 readings | L* | 51.97 | A* | 12.09 | B* | 12.03 |
| Sample #2 readings | L* | 50.61 | A* | 11.32 | B* | 14.70 |
| Sample #3 readings | L* | 53.21 | A* | 7.01 | B* | 14.03 |
| Sample #4 readings | L* | 59.6 | A* | 3.21 | B* | 13.82 |

Example VII

Four samples each of 320 grams of chicken breast Heritage Farm™ brand, were prepared as follows:
Sample 1. No (0% by weight) dried hemoglobin powder.
Sample 2. 1.0% by weight (3.2 grams) of dried bovine hemoglobin powder Sonac Harimix PB topically applied to meat.

Sample 3. 1/16% by weight (0.2 gram) dried bovine hemoglobin powder Sonac Harimix PB hydrated with 1 gram of water mixed and topically applied to meat.

Sample 4. No (0% by weight) dried hemoglobin powder.

Figure 7:
FIG. 7 is a photograph showing the results of Example VII.

Each sample was vacuum-sealed in a polymer package. Samples 2, 3 and 4 were then subjected to HPP treatment in an Avure QFP 525L-600 apparatus at about 72,000 psi and a temperature of about 38-40 degrees Fahrenheit for 60 seconds. Sample 1 was not HPP treated. The resulting packages are shown in FIG. 7. As you can see sample 1 has a natural poultry meat color, sample 2 has a similar to slightly lighter natural meat color, sample 3 is a lighter meat color than sample 2 and 1, sample 4 has a much lighter opaque to no color.

Each sample's color was checked and recorded using a Hunter Mini Scan XE spectrophotometer:

| | | | | | | |
|---|---|---|---|---|---|---|
| Sample #1 readings | $L^*$ | 41.04 | $A^*$ | 3.76 | $B^*$ | 1.33 |
| Sample #2 readings | $L^*$ | 52.00 | $A^*$ | 1.76 | $B^*$ | 18.76 |
| Sample #3 readings | $L^*$ | 63.78 | $A^*$ | 1.19 | $B^*$ | 14.39 |
| Sample #4 readings | $L^*$ | 68.22 | $A^*$ | -1.93 | $B^*$ | 9.24 |

These examples demonstrate that the application of hemoglobin to meat prior to HPP processing assists in preserving pleasant color in the meat. The use of hemoglobin to preserve the color of meats may be used with any variant of the HPP process. Typical parameters for the HPP process may be from about 10,000 to 100,000 psi pressure, and temperatures from about 32 degrees to about 50 degree Fahrenheit. The duration of application of pressure is usually 1 to 3 or several minutes, but less than an hour.

It will be appreciated that the process of the products, methods, and processes of the present application include the added benefit of fortifying the meat with iron.

It should be understood that the present application covers the following processes: (1) using animal blood, separating hemoglobin from the blood, while some red blood cells may or may not remain, converting the hemoglobin into a dried form, hydrating the dried hemoglobin, mixing the hydrated hemoglobin with meat, and subjecting the treated meat to a selected and controlled HPP process; (2) using animal blood, separating hemoglobin from the blood, mixing the undried hemoglobin with meat, and subjecting the treated meat to a selected and controlled HPP process; and (3) using animal blood, separating hemoglobin from the blood, mixing the hemoglobin, either in dry form or liquid form, mixing other color-retaining ingredients and/or agents into the meat, and subjecting the treated meat to a selected and controlled HPP process.

It is apparent that a system with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and/or combined, and all such variations are considered within the scope and spirit of the application. Accordingly, the protection sought herein is as set forth in the description.

Although the present embodiments are shown above, they are not limited to just these embodiments, but are amenable to various changes and modifications without departing from the spirit thereof.

The invention claimed is:

1. A method of pressure treating fresh meat, comprising:
    applying stabilized hemoglobin, prepared by spray drying, without other active ingredients to the fresh meat in an amount of about 0.08 to about 3% by weight of the fresh meat;
    thereafter sealing the fresh meat in a container; and
    thereafter pressure treating the fresh meat by application of pressure to the fresh meat at a sufficiently high pressure, a controlled temperature, and for a duration of time sufficient to rupture the cell walls of at least some microorganisms present in the fresh meat.

2. The method according to claim 1, wherein the fresh meat is selected from the group consisting of beef, pork, bison, lamb, veal, poultry and seafood.

3. The method according to claim 1, wherein the hemoglobin is a stabilized powder.

4. The method according to claim 1, wherein the pressure is applied isostatically at a pressure up to about 100,000 psi.

5. The method according to claim 1, further comprising:
    placing the fresh meat in a sealed, flexible container prior to the pressure treating step.

6. The method according to claim 1, wherein the hemoglobin is applied to an exterior surface of fresh muscle meat.

7. The method according to claim 1, wherein the hemoglobin is applied by mixing it with fresh ground meat.

8. The method according to claim 1, wherein the hemoglobin is in a liquid form.

9. The method according to claim 8, wherein the liquid hemoglobin has been dried and then rehydrated.

10. The method according to claim 1, wherein the hemoglobin contains red blood cells.

11. A method of isostatically pressure treating fresh meat to reduce the presence of pathogens and harmful bacteria on and in the fresh meat while seeking to preserve the natural color of the fresh meat, comprising:
    applying a stabilized hemoglobin, prepared by spray drying, to the fresh meat in an amount of about 0.08 to 1.0% by weight of the fresh meat, wherein the hemoglobin is without other active ingredients;
    thereafter sealing the fresh meat in a flexible container; and
    thereafter isostatically pressure treating the fresh meat by application of pressure to the fresh meat while sealed in the flexible container at a level of pressure of from 10,000 to 100,000 PSI, at a controlled temperature, and for a duration of time sufficient to rupture the cell walls of microorganisms present in the fresh meat.

12. The method of claim 11, wherein the hemoglobin is applied to an exterior surface of the fresh muscle meat.

13. The method of claim 11, wherein the hemoglobin is applied by mixing with fresh ground meat.

14. The method of claim 11, wherein the fresh meat is selected from the group consisting of beef, pork, bison, lamb, veal, poultry, and seafood.

15. The method of claim 11, wherein the duration of time is at least 60 seconds.

16. The method of claim 1, wherein the duration of time is at least 60 seconds.

* * * * *